United States Patent [19]
Westermann et al.

[11] Patent Number: 4,859,231
[45] Date of Patent: Aug. 22, 1989

[54] (6,7-)DIHYDRO-(1,2,4) TRIAZOLO (1,5-A) (1,3,5) TRIAZINE-2-SULPHONAMIDES, AND THEIR USE AS HERBICIDES AND PLANT GROWTH REGULATORS

[75] Inventors: Jürgen Westermann; Martin Krüger; Friedrich Arndt; Richard Rees; Clemens Kötter, all of Berlin, Fed. Rep. of Germany

[73] Assignee: Schering Aktiengesellschaft, Fed. Rep. of Germany

[21] Appl. No.: 135,142

[22] Filed: Dec. 18, 1987

[30] Foreign Application Priority Data

Dec. 19, 1986 [DE] Fed. Rep. of Germany ....... 3644343

[51] Int. Cl.⁴ .................... C07D 487/04; A01N 43/66
[52] U.S. Cl. .......................... 71/93; 71/90; 544/211; 544/212; 544/113
[58] Field of Search ..................... 71/90, 93; 544/211, 544/212, 113

[56] References Cited
U.S. PATENT DOCUMENTS 4,565,815 1/1986 Kim et al. ............................ 544/212

Primary Examiner—John M. Ford
Attorney, Agent, or Firm—Ostrolenk, Faber, Gerb & Soffen

[57] ABSTRACT

The invention relates to new 6,7-dihydro-[1,2,4] triazolo-[1,5-a][1,3,5]triazine-2-sulphonamides of general formula I

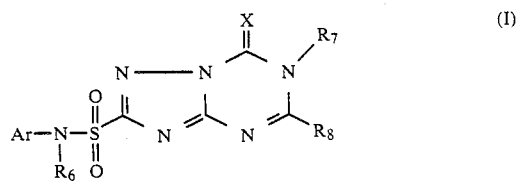

in which Ar, $R_6$, $R_7$, $R_8$ and X have the meanings given in the description, processes from their preparation and their use as herbicides and plant growth regulants.

20 Claims, No Drawings

(6,7-)DIHYDRO-(1,2,4) TRIAZOLO (1,5-A) (1,3,5) TRIAZINE-2-SULPHONAMIDES, AND THEIR USE AS HERBICIDES AND PLANT GROWTH REGULATORS

The invention relates to new 6,7-dihydro-[1,2,4]-triazolo[1,5-a][1,3,5]triazine-2-sulphonamides, processes for their preparation and their use as herbicides and plant growth regulators.

It is known that triazolopyrimidinesulphonamides possess herbicidal activity (EP 142 152 and 150 974). However the herbicidal activity of the known compounds is not sufficient and/or selectivity problems can occur in important crops.

The object of the present invention is to make new compounds that do not show the disadvantages of the known compounds and have improved biological properties.

It has now been found that 6,7-dihydro-[1,2,4]triazolo-[1,5-a][1,3,5]triazine-2-sulphonamides of general formula I

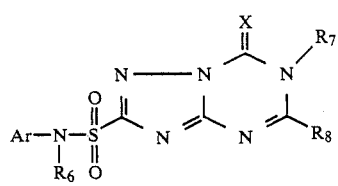

in which
Ar is a phenyl, naphthyl, pyridyl or thienyl group of general formula

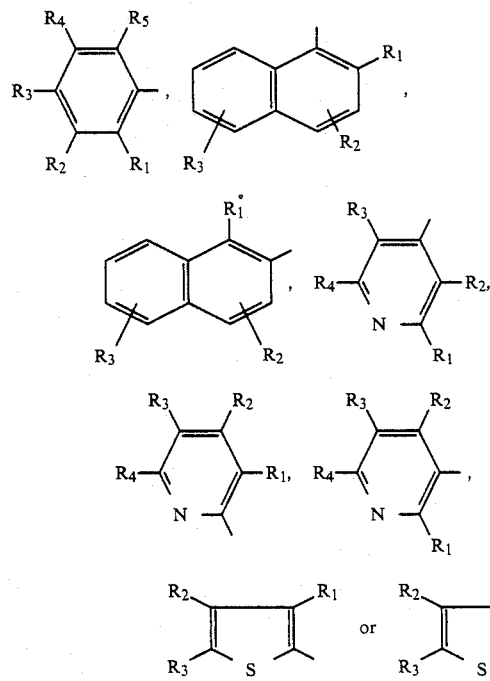

$R_1$, $R_2$, $R_3$, $R_4$ and $R_5$ are the same or different and are hydrogen, a $C_1$-$C_6$-alkyl, $C_2$-$C_6$-alkenyl or $C_2$-$C_6$-alkynyl group, each of which is optionally substituted by one or more of the same or different halo, hydroxy, halo-$C_1$-$C_4$-alkyl, $C_1$-$C_4$-alkoxy, halo-$C_1$-$C_4$-alkoxy, $C_1$-$C_4$-alkylthio, $C_1$-$C_4$-alkylsulphinyl or $C_1$-$C_4$-alkyl-sulphonyl, halogen, $C_1$-$C_4$-alkoxy, a group $R_9$—O—CO, a carbamoyl group

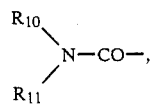

an amino group

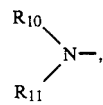

cyano, nitro, a sulphur containing group $R_9$—S(O)$_n$—, an acyl group $R_9$—CO, a group $R_9$—O—CO—(CH$_2$)$_n$, or phenyl or phenoxy, both of which are optionally substituted by one or more of $C_1$-$C_4$-alkyl, halo or nitro, $R_6$ is hydrogen, an acyl group $R_9$—CO, a group $R_9$—O—CO—, $C_1$-$C_6$-alkyl, $C_2$-$C_6$-alkenyl, $C_2$-$C_6$-alkynyl, phenyl-$C_1$-$C_4$-alkyl, a carbamoyl group

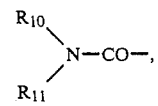

an alkali metal atom, a single metal equivalent of an alkaline earth or other metals or ammonium group, optionally substituted by $C_1$-$C_3$-alkyl, $R_7$ and $R_8$ are the same or different and are hydrogen, a $C_1$-$C_6$-alkyl, $C_2$-$C_6$-alkenyl or $C_2$-$C_6$-alkynyl group, each of which is optionally substituted by halo and/or $C_1$-$C_4$-alkoxy, a phenyl-$C_1$-$C_6$-alkyl, phenyl-$C_2$-$C_6$-alkenyl or phenyl-$C_2$-$C_6$-alkynyl group, each of which is optionally substituted by halo, $C_1$-$C_4$-alkyl, $C_1$-$C_4$-alkoxy, $C_1$-$C_4$-alkoxy-$C_1$-$C_4$-alkyl or halo-$C_1$-$C_4$-alkyl, phenyl, substituted by $R_1$, $R_2$, $R_3$, $R_4$ and $R_5$, an acyl group $R_9$—CO, a group $R_9$—O—CO, a group $R_9$—O—CO—(CH$_2$)$_n$, a carbamoyl group

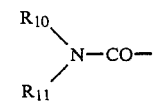

or a sulphonyl group $R_9$—SO$_2$, $R_9$ is hydrogen, a $C_1$-$C_6$-alkyl, $C_2$-$C_6$-alkenyl, $C_2$-$C_6$-alkynyl or phenyl-$C_1$-$C_4$-alkyl group, each of which is optionally substituted by one or more of the same or different halo, hydroxy or $C_1$-$C_4$-alkoxy, or phenyl, optionally substituted by halo, nitro or $C_1$-$C_4$-alkyl, $R_{10}$ and $R_{11}$ are the same or different and are hydrogen, a $C_1$-$C_6$-alkyl, $C_2$-$C_6$-alkenyl or $C_2$-$C_6$-alkynyl group, each of which is optionally substituted by one or more of the same or different halo, hydroxy or $C_1$-$C_4$-alkoxy, or $R_{10}$ and $R_{11}$ together with the adjacent nitrogen form a pyrrolidinyl, piperidino or morpholino ring, X is oxygen or sulphur, and n is 0, 1 or 2, show an interesting herbicidal and plant growth regulant activity.

The term "halogen" in relationship with alkyl, alkenyl, alkynyl or phenyl means that one or more hydrogen atoms are replaced by one or more halogen atoms.

The term "halogen" means fluorine, chlorine, bromine and iodine.

6,7-Dihydro-[1,2,4]triazolo[1,5-a][1,3,5]triazine-2-sulphonamides of general formula I which show particularly good activity are those in which Ar is a phenyl group of general formula

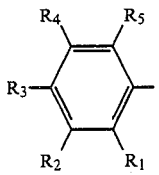

$R_1$ and $R_5$ are the same or different and are halogen, methyl, trifluoromethyl, nitro, methoxy or methoxycarbonyl, $R_2$, $R_3$ and $R_4$ are the same or different and are hydrogen, halogen, trifluoromethyl or a $C_1-C_4$-alkyl group, $R_6$ is hydrogen, a single equivalent of a metal or a $C_1-C_4$-acyl group, and $R_7$ and $R_8$ are the same or different and are hydrogen, $C_1-C_4$-acyl, $C_1-C_6$-alkyl, $C_2-C_4$-alkenyl or phenyl.

The compounds of the invention of general formula I can be prepared for example by (A) reacting an amine of general formula II,

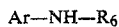
Ar—NH—R$_6$ (II)

in which Ar has the meaning given above and $R_6$ is hydrogen, $C_1-C_6$-acyl, $C_2-C_6$-alkenyl or $C_2-C_6$-alkynyl, with a sulphonyl chloride of general formula III

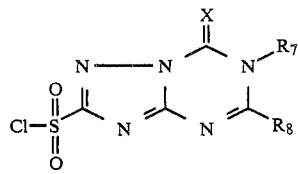

in which $R_7$, $R_8$ and X have the meanings given above in a suitable solvent and in the presence of an acid acceptor, or (B) reacting a compound of general formula IV

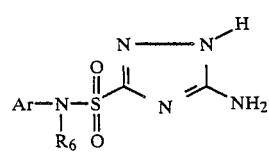

in which Ar has the meaning given above and $R_6$ is hydrogen, $C_1-C_6$-acyl, $C_2-C_6$-alkenyl or $C_2-C_6$-alkynyl, with an isocyanate or isothiocyanate of formula V

R$_7$—NCX (V)

in which $R_7$ and X have the meanings given above in a suitable solvent, optionally in the presence of an acid acceptor and/or catalyst, and reacting the resulting compound of general formula VI

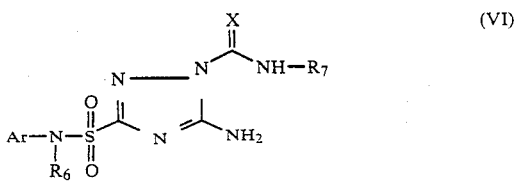

in which Ar, $R_7$ and X have the meanings given above and $R_6$ is hydrogen, $C_1-C_6$-acyl, $C_2-C_6$-alkenyl or $C_2-C_6$-alkynyl, with an ortho ester of general formula VII

$R_8$—C(OR$_9$)$_3$ (VII)

in which $R_9$ has the meaning given above, except hydrogen, and $R_8$ is hydrogen, a $C_1-C_6$-alkyl, $C_2-C_6$-alkenyl or $C_2-C_6$-alkynyl group, each of which is optionally substituted by halo and/or $C_1-C_4$-alkoxy, a phenyl-$C_1-C_6$-alkyl, phenyl-$C_2-C_6$-alkenyl or phenyl-$C_2-C_6$-alkynyl group, each of which is optionally substituted by halo, $C_1-C_4$-alkyl, $C_1-C_4$-alkoxy, $C_1-C_4$-alkoxy-$C_1-C_4$-alkyl or halo-$C_1-C_4$-alkyl, or phenyl, substituted by $R_1$, $R_2$, $R_3$, $R_4$ and $R_5$, in a suitable solvent, which can be the orthoester itself, or (C) reacting a compound of general formula IV

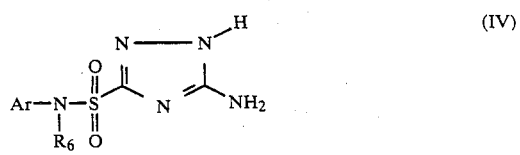

in which Ar has the meaning given above and $R_6$ has the meaning given under (B), with an ortho ester of general formula VII

$R_8$—C(OR$_9$)$_3$ (VII)

in which $R_8$ and $R_9$ have the meanings given under (B), in a suitable solvent, which can be the orthoester itself, to give a compound of formula VIII

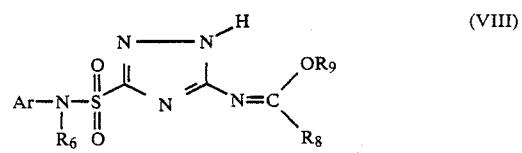

which is reacted with an isocyanate or isothiocyanate of formula V

R$_7$—NCX (V)

in which $R_7$ and X have the meanings given above in a suitable solvent, optionally in the presence of an acid acceptor and/or catalyst, or (D) reacting a compound of general formula IX

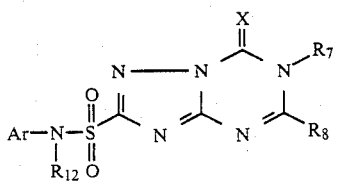

(IX)

in which Ar, $R_7$, $R_8$ and X have the meanings given above and $R_{12}$ is hydrogen or a single equivalent of a metal, with a compound of general formula X $$R_9\text{—Hal} \qquad (X)$$

or of general formula XI $$R_9\text{—CO—Hal} \qquad (XI)$$

in which $R_9$ has the meaning given above, except hydrogen and Hal is chlorine or bromine, or of general formula XII $$R_9\text{—CO—O—COR}_9 \qquad (XII)$$

in which $R_9$ has the meaning given above, in a suitable solvent, or (E) reacting a compound of general formula XIII

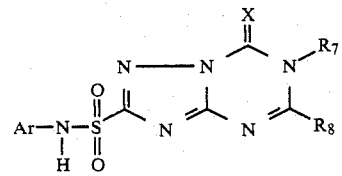

(XIII)

in which Ar, $R_7$, $R_8$ and X have the meanings given above, with a compound of general formula XIV $$M\text{—Y} \qquad (XIV)$$

in which M is a single equivalent of a metal, and Y is hydrogen, hydroxy, lower alkyl, lower alkoxy or an amino group, in a suitable solvent.

The particular reaction variants are preferably carried out in the presence of a diluent. For this purpose there are used solvents which are inert to the reactants.

Examples of such solvents or diluents are water, aliphatic, alicyclic and aromatic hydrocarbons, that can optionally be chlorinated, such as for example hexane, cyclohexane, petroleum ether, ligroin, benzene, toluene, methylene chloride, chloroform, carbon tetrachloride, ethylene dichloride and trichloroethane, ethers, such as for example diisopropyl ether, dibutyl ether, propylene oxide, dioxane and tetrahydrofuran, ketones such as for example acetone, methyl ethyl ketone, methyl isopropyl ketone and methyl isobutyl ketone, nitriles, such as for example acetonitrile and propionitrile, alcohols, such as for example methanol, ethanol, isopropanol, butanol and ethylene glycol, esters, such as for example ethyl acetate and amyl acetate, amides, such as for example dimethylformamide and dimethylacetamide, sulphones and sulphoxides, such as for example dimethyl sulphoxide and and sulpholane, and bases, such as for example pyridine.

The reaction is suitably carried out between room temperature and the boiling point of the particular reaction mixture. The reaction can be carried out under atmospheric pressure but if desired higher or lower pressures can be used.

Process variant A is preferably carried out in chlorinated hydrocarbons, such as dichloromethane or dichloroethane, in the presence of a catalyst and and/or acid acceptor. Examples of these are tertiary amines such as for example triethylamine, diisopropylethylamine, N-methylmorpholine, 4-dimethylaminopyridine and pyridine. Pyridine can be used both as catalyst and as solvent.

Process variants B and C are preferably carried out in diluents such as, aliphatic, alicyclic and aromatic hydrocarbons, that can optionally be chlorinated, such as for example hexane, cyclohexane, petroleum ether, ligroin, benzene, toluene, methylene chloride, chloroform, carbon tetrachloride, ethylene dichloride and trichloroethane, ethers, such as for example diisopropyl ether, dibutyl ether, propylene oxide, dioxane and tetrahydrofuran, ketones such as for example acetone, methyl ethyl ketone, methyl isopropyl ketone and methyl isobutyl ketone, nitriles, such as for example acetonitrile and propionitrile, esters, such as for example ethyl acetate and amyl acetate, amides, such as for example dimethylformamide and dimethylacetamide, sulphones and sulphoxides, such as for example dimethyl sulphoxide and and sulpholane, and bases, such as for example pyridine, and optionally in the presence of a catalyst and and/or acid acceptor. Examples of these are tertiary amines such as for example triethylamine, diisopropylethylamine, N-methylmorpholine, 4-dimethylamino pyridine and pyridine.

Process variant D is preferably carried out by reacting a compound of general formula IX in a suitable solvent with a compound of general formula X, XI or XII, filtering off the salts which as general rule are highly insoluble and recovering the desired compounds after evaporation of the solvent.

Process variant E is preferably carried out by reacting a compound of general formula XIII in a suitable solvent with a metal base, such as a metal hydroxide, metal hydride, metal alkyl or metal amide, and the salts which as a general rule are highly insoluble can be recoverd by filtration or by evaporation of the solvent.

The compounds of the invention prepared by these processes can be isolated from the reaction mixtures in conventional manner, for example by distillation of the solvent at normal or reduced pressure, by precipitation with water or by extraction.

A higher level of purity can be achieved as a rule by column chromatography as well as by fractional distillation or crystallisation.

The compounds of the invention are, as a rule, colorless or odourless crystals that are slightly soluble in water and in aliphatic hydrocarbons such as petroleum ether, hexane, pentane and cyclohexane and highly soluble in halogenated hydrocarbons, such as chloroform, methylene chloride and carbon tetrachloride, aromatic hydrocarbons such as benzene, toluene and xylene, ethers, such as diethyl ether, tetrahydrofuran and dioxane, nitriles, such as acetonitrile, alcohols, such as methanol and ethanol, amides, such as dimethylformamide, and sulphoxides, such as dimethyl sulphoxide.

The sulphonyl chlorides of general formula III are new and can be prepared as described in the literature or by known methods by reacting a 2-benzylthio-6,7-dihydro-[1,2,4]triazole[1,5-a][1,3,5]triazin-7-one of general formula XV

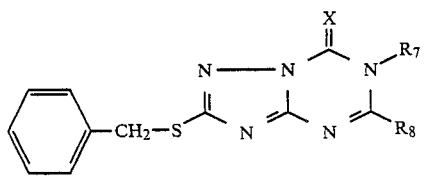

in which R<sub>7</sub>, R<sub>8</sub> and X have the meanings given above, with chlorine in water or a water/acetic acid mixture.

Amines of general formula II, isocyanates and isothiocyanates of general formula V and orthoesters of general formula VII are in the main commercially available or can be prepared by known processes or as described in the literature.

The compounds of the invention influence plant growth and can therefore be used as plant growth regulators and especially as herbicides. Surprisingly, the compounds of the invention show a wide activity against monocotyledonous and dicotyledonous weeds with good selectivity in crops. Whether the compounds of the invention act as total or selective herbicides depends mainly on the rates of use but also on the species and the time of use.

The compounds can be used in seed treatments, and in pre or post emergent use.

The compounds of the invention can used for example against the following plant species: Dicotyledonous weeds of the species Polygonum, Sinapis, Atriplex, Spergula, Stellaria, Galium, Viola, Cirsium, Amaranthus, Ipomoea, Xanthium, Abutilon, Chenopodium, Cassia, Convolvulus, Mentha, Veronica, Matricaria, Solanum, Lamium, Thlapsi, Capsella, Datura, Galinsoga, Mercurialis, Rhaphanus, Vicia, Portulaca, Physalis, Sida, Anoda, Euphorbia, Myosotis, Centaurea, Brassica, Chrysanthemum and Helianthus; Monocotyledonous weeds of the species Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Agrostis, Alopecurus, Apera, Rottboellia, Triticum and Hordeum.

The compounds can be used in important agricultural crops, such as wheat, barley, rice and soya beans.

The use of the compounds of the invention is not limited to the weeds and crops mentioned above but can also be applied in a similar way to other plants.

The compounds are also suitable for weed control in industrial and railway installations and also roads and verges, with or without vegetation, in forests, woodlands, berry fruit and hop installations as well as plantations.

The rates of use can vary over a wide range. They depend generally on the nature of the desired effects. In general the rates of use lie between 0.01 and 5 kg of active ingredient per hectare and preferably for example in weed control between 0.1 and 0.5 kg of active ingredient per hectare.

The compounds of the invention can be used either alone or in admixture with one another or with other active agents. Optionally, other plant-protective agents or pesticides can be added, depending on the purpose for the treatment. When it is desired to broaden the spectrum of activity, other herbicides can also be added. Herbicidally active mixing partners suitable in this connection include for example, the active agents listed in Weed Abstracts, vol. 34, No. 5 (1986) under the heading "Lists of common names and abbreviations employed for currently used herbicides and plant growth regulators in Weed Abstracts".

An improvement in the intensity and speed of action can be obtained, for example, by addition of suitable adjuvants, such as organic solvents, wetting agents and oils. Such additives may allow a decrease in the dose.

Suitable mixture partners may include phospholipids, e.g. phosphatidylcholine, hydrated phosphatidylcholines phosphatidylethanolamine, N-acyl-phosphatidylethanolamines, phosphatidylinositol, phosphatidylserine, lysolecithin or phosphatidylglycerol.

The designated active ingredients or their mixtures can suitable be used, for example, as powders, dusts, granules, solutions, emulsions or suspensions, with the addition of liquid and/or solid carriers and/or diluents and, optionally, binding, wetting, emulsifying and/or dispersing adjuvants.

Suitable liquid carriers are, for example aliphatic and aromatic hydrocarbons, such as benzene, toluene, xylene, cyclohexanone, isophorone, dimethyl sulphoxide, dimethylformamide and other mineral-oil fractions and plant oils.

Suitable solid carriers include mineral earths, e.g. bentonite, silica gel, talcum, kaolin, attapulgite, limestone, silicic acid and plant products, e.g. flours.

As surface-active agents there can be used for example calcium lignosulphonate, polyoxyethylenealkylphenyl ether, naphthalenesulphonic acids and their salts, phenolsulphonic acids and their salts, formaldehyde condensates, fatty alcohol sulphates, as well as substituted benzenesulphonic acids and their salts.

The percentage of the active ingredient(s) in the various preparations can vary within wide limits. For example, the compositions can contain about 10 to 90 percent by weight active ingredients, and about 90 to 10 percent by weight liquid or solid carriers, as well as, optionally up to 20 percent by weight of surfactant.

The agents can be applied in customary fashion, for example with water as the carrier in spray mixture volumes of approximately 100 to 1,000 l/ha. The agents can be applied using low-volume or ultra-low-volume techniques or in the form of so-called microgranules.

The preparation of these formulations can be carried out in known manner, for example by milling or mixing process. Optionally, individual components can be mixed just before use for example by the so-called commonly used tank-mixing method.

Formulations can be prepared, for example, from the following ingredients.

(A) Wettable Powder (1)
25 percent by weight active ingredient
60 percent by weight kaolin
10 percent by weight silicic acid
5 percent by weight of a mixture of calcium lignosulphonate and the sodium salt of N-methyl-N-oleyltaurine (2)
40 percent by weight active ingredient
25 percent by weight bentonite
25 percent by weight colloidal silicic acid
10 percent by weight of a mixture of calcium lignosulphonate and alkylphenyl polyglycol ether (B) Paste 45 percent by weight active ingredient
5 percent by weight sodium aluminium silicate
15 percent by weight cetyl polyglycol ether with 8 mol of ethylene oxide
2 percent by weight spindle oil
10 percent by weight polyethylene glycol
23 percent by weight water (C) Emulsifiable Concentrate 25 percent by weight active ingredient
15 percent by weight cyclohexanone
55 percent by weight xylene
5 percent by weight of a mixture of calcium dodecylbenzenesulphonate and nonylphenolpolyoxyethylene.

The following examples illustrate the preparation of compound according to the invention.

EXAMPLE 1

N-(2,6-Dichlorophenyl)-6,7-dihydro-N,5,6-trimethyl-7-oxo[1,2,4]triazolo[1,5-a][1,3,5]triazine-2-sulphonamide (Process B)

1.30 g (3.4 mmol) 5-Amino-N-(2,6-dichlorophenyl)-N-methyl-1-(methylcarbamoyl)-1,2,4-triazole-3-sulphonamide was stirred in 10 ml triethyl orthoacetate with 5 drops glacial acetic acid for 12 hours at 120° C. The insoluble residue was filtered and the filtrate concentrated. The product was chromatographed on silica gel using a mixture of hexane and ethyl acetate.

Yield: 0.77 g=56% of theory; M.p.: 286°–288° C.

| Elementary analysis | | | | | |
|---|---|---|---|---|---|
| Calc. (%): | C 38.72 | H 3.00 | N 20 84 | S 7.95 | Cl 17.58 |
| Found (%): | C 38.54 | H 3.10 | N 20.79 | S 8.01 | Cl 17.59 |

Preparation of the Starting Material for Example 1

(a)

5-Amino-N-(2,6-dichlorophenyl)-N-methyl-1-(N-methylcarbamoyl)-1,2,4-triazole-3-sulphonamide 2.0 g (6.2 mmol) 5-Amino-N-(2,6-dichlorophenyl)-N-methyl-1,2,4-triazole-3-sulphonamide was suspended in 30 ml tetrahydrofuran and treated with 0.5 ml (8.5 mmol) methyl isocyanate and 0.9 ml (6.5 mmol) triethylamine. The mixture was stirred for 3 hours at room temperature and allowed to stand overnight. The solution was concentrated and the residue chromatographed on silica gel using a mixture of hexane and ethyl acetate.

Yield: 1.36 g=58% of theory; M.p.: 220°–222° C.

| Elementary analysis | | | | | |
|---|---|---|---|---|---|
| Calc. (%): | C 34.84 | H 3.19 | N 22.16 | S 8.46 | Cl 18.70 |
| Found (%): | C 34.80 | H 3.64 | N 21.99 | S 8.13 | Cl 18.33 |

(b)

5-Amino-N-(2,6-dichlorophenyl)-N-methyl-1,2,4-triazole-3-sulphonamide 9.80 g (22.8 mmol) of the pyridine salt of 1-acetyl-5-amino-N-(2,6-dichlorophenyl)-1,2,4-triazole-3-sulphonamide was dissolved in 300 ml dimethylformamide and 0.89 g (29.7 mmol) 80% sodium hydride added portionwise at room temperature. The mixture was stirred for a further 30 minutes and 1.7 ml (27.8 mmol) methyl iodide added. The mixture was allowed to stand overnight and concentrated. The residue was taken up in 2N aqueous sodium hydroxide and made slightly acidic by addition of 3N hydrochloric acid. The crystals were separated, washed with water and ether and recrystallised from acetonitrile.

Yield: 3.4 g=46% of theory; M.p.: 254°–255° C.

| Elementary analysis | | | | | |
|---|---|---|---|---|---|
| Calc. (%): | C 33.55 | H 2.82 | N 21.74 | S 9.95 | Cl 22.01 |
| Found (%): | C 34.80 | H 3.10 | N 21.63 | S 10.08 | Cl 22.18 |

EXAMPLE 2

N-(2,6-Dichlorophenyl)-6,7-dihydro-5,6-dimethyl-7-oxo[1,2,4]triazole[1,5-a][1,3,5]triazine-2-sulphonamide (2.1 by process variant C)

3.4 g (9.0 mmol) N-(2,6-Dichlorophenyl)-5-(1-ethoxyethylidenamino)-1H-1,2,4-triazole-3-sulphonamide was stirred in 70 ml tetrahydrofuran with 0.66 ml (11.3 mmol) methyl isocyanate and 1.3 ml (9.3 mmol) triethylamine for 4 hours at room temperature. The crystals were separated, washed with tetrahydrofuran/water 4:1, tetrahydrofuran and ether and dried in vacuo.

Yield: 3.4 g=97% of theory; M.p.: 331°–334° C.

| Elementary analysis | | | | | |
|---|---|---|---|---|---|
| Calc. (%): | C 37.03 | H 2.59 | N 21.59 | S 8.24 | Cl 18.22 |
| Found (%): | C 37.21 | H 2.60 | N 21.22 | S 8.54 | Cl 18.35 |

(2.2 by process variant A)

0.88 g (5.4 mmol) 2,6-Dichloroaniline was dissolved in 11 ml pyridine and treated with 1.67 g (6.0 mmol) 6,7-dihydro-5,6-dimethyl-7-oxo-[1,2,4]triazole[1,5-a][1,3,5]triazine-2-sulphonyl chloride. The mixture was stirred for 11 hours at 50° C. and for 5 hours at 75° C. The pyridine was distilled and the residue chromatographed with hexane/ethyl acetate.

Yield: 0.23 g=10% of theory; M.p.: 331°–334° C.

Preparation of the Starting Material for Example 2.1

(a)

N-(2,6-Dichlorophenyl)-5-(1-ethoxyethylidenamino)-1H-1,2,4-triazole-3-sulphonamide 6.16 g (20.0 mmol) 5-amino-N-(2,6-dichlorophenyl)-1H-1,2,4-triazole-3-sulphonamide was heated in 50 ml acetonitrile with 4.2 ml (23.0 mmol) triethyl orthoacetate and 3 drops glacial acetic acid for 5 hours under reflux. The mixture was cooled and evaporated to dryness. The residue was recrystallized from ethyl acetate.

Yield: 6.1 g=80% of theory; M.p.: 222°–224° C.

| Elementary analysis | | | | | |
|---|---|---|---|---|---|
| Calc. (%): | C 38.10 | H 3.46 | N 18.52 | S 8.48 | Cl 18.75 |
| Found (%): | C 38.09 | H 3.63 | N 18.64 | S 8.57 | Cl 18.89 |

In a similar manner to these processes the following compounds were prepared.

| Name of Compound | Physical Constant |
|---|---|
| N—(2,6-Dichlorophenyl)-5-(1-ethoxymethylenamino)-1H—1,2,4-triazole-3-sulphonamide | mp: 181–183° C. |
| N—(2,6-Dichlorophenyl)-5-(1-ethoxypropylidenamino)-1H—1,2,4-triazole-3-sulphonamide | mp: 212–216° C. |
| N—(2,6-Dichlorophenyl)-5-(1-ethoxybenzylidenamino)-1H—1,2,4-triazole-3-sulphonamide | mp: 213–217° C. |
| N—(2,6-Dichloro-3-methylphenyl)-5-(1-ethoxyethylidenamino)-1H—1,2,4-triazole-3-sulphonamide | mp: 202–204° C. |
| 5-(1-Ethoxyethylidenamino)-N—(2-methyl-6-nitrophenyl)-1H—1,2,4-triazole-3-sulphonamide | mp: 195–197° C. |
| N—(2-Chloro-6-fluorophenyl)-5-(1-ethoxyethylidenamino)-1H—1,2,4-triazole-3-sulphonamide | mp: 214–215° C. |
| 5-(1-Ethoxyethylidenamino)-N—(2,6-difluorophenyl)-1H—1,2,4-triazole-3-sulphonamide | mp: 187–188° C. |
| N—(2,6-Dibromophenyl)-5-(1-ethoxyethylidenamino)-1H—1,2,4-triazole-3-sulphonamide | mp: 184–187° C. |
| 5-(1-Ethoxyethylidenamino)-N—(2-trifluorophenyl)-1H—1,2,4-triazole-3-sulphonamide | mp: 124–125° C. |
| 5-(1-Ethoxyethylidenamino)-N—phenyl-1H—1,2,4-triazole-3-sulphonamide | mp: 164–166° C. |
| N—(2-Chlorophenyl)-5-(1-ethoxyethylidenamino)-1H—1,2,4-triazole-3-sulphonamide | mp: 150–153° C. |
| 5-(1-Ethoxyethylidenamino)-N—(2-methoxyphenyl)-1H—1,2,4-triazole-3-sulphonamide | mp: 134–140° C. |

(b)
5-Amino-N-(2,6-dichlorophenyl)-1,2,4-triazole-3-sulphonamide 53.6 g (0.12 mol) of the pyridine salt of 1-acetyl-5-amino-N-(2,6-dichlorophenyl)-1,2,4-triazole-3-sulphonamide was dissolved in 200 ml 2N aqueous sodium hydroxide and stirred at room temperature for 10 minutes. With ice cooling it was brought to pH 5 with 2N hydrochloric acid. The crystals were separated, washed with a small amount of water and ether and dried in vacuo.

Yield: 35.4 g=92% of theory; M.p.: 265°–267° C.

| Elementary analysis | | | | | |
|---|---|---|---|---|---|
| Calc. (%): | C 31.18 | H 2.29 | N 22.73 | S 10.41 | Cl 23.0 |
| Found (%): | C 31.38 | H 2.40 | 22.37 | S 10.23 | Cl 22.23 |

(c)
1-Acetyl-5-amino-N-(2,6-dichlorophenyl)-1,2,4-triazole-3-sulphonamide 42.63 g (0.26 mol) 2,6-dichloroaniline in 350 ml pyridine was treated with 54 g (0.24 mol) of 1-acetyl-5-amino-1,2,4-triazole-3-sulphonyl chloride and stirred at 60° C. for 12 hours. After cooling, the crystals were separated, washed with a small amount of pyridine and ether and dried in vacuo.

Yield: 53.6 g=52% of theory; M.p.: 213°–215° C.

| Elementary analysis | | | | | |
|---|---|---|---|---|---|
| Calc. (%): | C 41.96 | H 3.29 | N 19.58 | S 7.47 | Cl 16.52 |
| Found (%): | C 41.89 | H 3.33 | N 19.36 | S 7.46 | Cl 15.97 |

(d) 1-Acetyl-5-amino-1,2,4-triazole-3-sulphonyl chloride 42.63 g (0.26 mol) 1-Acetyl-5-amino-3-benzylthio-1,2,4-triazole was suspended in 1 liter water/acetic acid (1:1 mixture). At −10° C. chlorine was introduced over 2 hours at a such a rate that that the inner temperature remained below 0° C. The resulting crystals were separated, washed with a small amount of water and pentane and dried.

Yield: 74.5 g=73.5% of theory; M.p.: 166°–168° C.

(e) 1-Acetyl-5-amino-3-benzylthio-1,2,4-triazole

To 30 g (0.145 mol) 5-amino-3-benzylthio-1H-1,2,4-triazole and 25 ml triethylamine in 300 ml methylene chloride, 12.57 g (0.16 mol) acetyl chloride in 30 ml methylene chloride was added dropwise. It was then stirred at room temperature for 30 minutes, treated with 160 ml 1N caustic soda and the product extracted with methylene chloride. After drying it was recrystallised from ethyl acetate.

Yield: 33 g=91% of theory; M.p.: 146° C.

| Elementary analysis | | | | |
|---|---|---|---|---|
| Calc. (%): | C 53.20 | H 4.87 | N 22.56 | S 12.91 |
| Found (%): | C 53.51 | H 5.36 | N 22.81 | S 12.81 |

(f) 1-Amino-3-benzylthio-1,2,4-triazole 40.36 g (0.35 mol) 3-Amino-5-mercapto-1H-1,2,4-triazole in 450 ml ethanol was treated with 13.9 g solid sdium hydroxide at room temperature. At room temperature, 44.30 g (0.35 mol) benzyl chloride chloride was added dropwise and the solution stirred overnight. The salt was filtered off, ethanol distilled and the residue recrystallised from ethyl acetate and dried.

Yield: 64.97 g=90% of theory; M.p.: 104° C.

| Elementary analysis | | | | |
|---|---|---|---|---|
| Calc. (%): | C 52.40 | H 4.88 | N 27.16 | S 15.54 |
| Found (%): | C 52.10 | H 4.84 | N 27.48 | S 15.11 |

PREPARATION OF THE STARTING MATERIAL FOR EXAMPLE 2.2

(a)
6,7-Dihydro-5,6-dimethyl-7-oxo-[1,2,4]triazolo[1,5-a]-[1,3,5]triazine-2-sulphonyl chloride 3.00 (10.04 mmol) 2-benzylthio-6,7-dihydro-5,6-dimethyl-[1,2,4]triazolo[1,5-a]-[1,3,5]triazin-7-one was suspended in 50 ml water/acetic acid (1:1 mixture). At 5° to 10° C., chlorine was introduced over 45 minutes and the stirred for one hour. The resulting crystals were separated, washed with a small amount of water and ether and dried at 50° C. in vacuo.

Yield: 2.22 g=80.7% of theory; M.p.: 206°–207° C.

| Elementary analysis | | | | | |
|---|---|---|---|---|---|
| Calc. (%): | C 27.33 | H 2.29 | N 26.56 | S 12.16 | Cl 13.45 |
| Found (%): | C 27.51 | H 2.69 | N 26.33 | S 12.13 | Cl 13.30 |

(b)

2-Benzylthio-6,7-dihydro-5,6-dimethyl-[1,2,4]triazolo-[1,5-a]-[1,3,5]triazin-7-one 8.50 g (30.8 mmol) 3-Benzylthio-5-(1-ethoxyethylidenamino)-1H-1,2,4]triazole was dissolved in 250 ml tetrahydrofuran and treated with 3.73 g (36.9 mmol) methyl isocyanate and 3.73 g (36.9 mmol) triethylamine. It was stirred for 5 hours at 70° C., the solvent distilled and the residue treated with ether. The crystals were separated and recrystallised from toluene.

Yield: 4.40 g=49.8% of theory; M.p.: 127°–128° C.

| Elementary analysis | | | | |
|---|---|---|---|---|
| Calc. (%): | C 54.34 | H 4.56 | N 24.27 | S 11.16 |
| Found (%): | C 54.30 | H 4.79 | N 24.33 | S 10.96 |

(c)

3-Benzylthio-5-(1-ethoxyethylidenamino)-1H-1,2,4]triazole 10.00 g (48.5 mmol) 5-amino-3-benzylthio-1H-1,2,4]triazole was suspended in 120 ml acetonitrile and reacted with 8 .38 g (53.3 mmol) triethyl orthoacetate and 3 drops glacial acetic acid. The mixture was heated for 6.5 hours under reflux, evaporated to dryness, taken up in hexane, with heating, filtered and again evaporated to dryness.

Yield: 10.89 g=81.3% of theory; M.p.: 89°–90° C.

| Elementary analysis | | | |
|---|---|---|---|
| Calc. (%): | C 56.50 | H 5.84 | N 20.27 | S 11.60 |
| Found (%): | C 56.59 | H 5.37 | N 20.58 | S 11.92 |

EXAMPLE 3

Triethylammonium salt of N-(2,6-dichlorophenyl)-6,7-dihydro-5,6-dimethyl-7-thioxo-[1,2,4]triazolo[1,5-a]-[1,3,5]triazine-2-sulphonamide (By process variant C)

7.56 g (0.02 mol) of (2,6-Dichlorophenyl)-5-(1-ethoxyethylidenamino)-N-1H-1,2,4-triazole-3-sulphonamide was treated in 70 ml tetrahydrofuran with 1.7 ml (0.025 mol) methyl isothiocyanate and 3.5 ml (0.025 mol) triethylamine and heated at 50° C. for 8 hours. The crystals were separated, washed with tetrahydrofuran and ether and dried in vacuo.

Yield: 5.4 g=53% of theory; M.p.: 217°–218° C.

| Elementary analysis | | | | | |
|---|---|---|---|---|---|
| Calc. (%): | C 42.68 | H 4.97 | N 19.36 | S 12.66 | Cl 14.00 |
| Found (%): | C 42.83 | H 4.82 | N 19.34 | S 12.69 | Cl 14.13 |

EXAMPLE 4

N-(2,6-Dichlorophenyl)-6,7-dihydro-5,6-dimethyl-7-thioxo-[1,2,4]triazolo[1,5-a[]1,3,5]triazine-2-sulphonamide 1.7 g (3.4 mol) of the triethylammonium salt of N-(2,6-dichlorophenyl)-6,7-dihydro-5,6-dimethyl-7-thioxo-[1,2,4]triazolo[1,5-a][1,3,5]triazine-2-sulphonamide was suspended in 100 ml water and acidified with 1N hydrochloric acid. The crystals were separated, washed with water and ether and dried in vacuo.

Yield: 1.3 g=94% of theory; M.p.: 301°–302° C.

| Elementary analysis | | | | | |
|---|---|---|---|---|---|
| Calc. (%): | C 35.56 | H 2.49 | N 20.74 | S 15.82 | Cl 17.50 |
| Found (%): | C 35.18 | H 2.70 | N 20.28 | S 16.19 | Cl 17.74 |

In a similar manner to the Examples 1 to 4 the following compounds of the invention were prepared.

| Example | Name of Compound | Physical Constant |
|---|---|---|
| 5 | N—(2,6-Dichloro-3-methylphenyl)-6,7-dihydro-5,6-dimethyl-7-thioxo-[1,2,4]triazolo[1,5-a]-[1,3,5]triazine-2-sulphonamide | mp: 241–242° C. |
| 6 | 6,7-Dihydro-5,6-dimethyl-N—(2-methyl-6-nitrophenyl)-7-thioxo-[1,2,4]triazolo-[1,5-a][1,3,5]triazine-2-sulphonamide | mp: 242–244° C. |
| 7 | N—(2-Chloro-6-fluorophenyl)-6,7-dihydro-5,6-dimethyl-7-thioxo-[1,2,4]triazolo[1,5-a]-[1,3,5]triazine-2-sulphonamide | mp: 274–275° C. |
| 8 | N—(2,6-Difluorophenyl)-6,7-dihydro-5,6-dimethyl-7-thioxo-[1,2,4]triazolo[1,5-a]-[1,3,5]triazine-2-sulphonamide | mp: 284–285° C. |
| 9 | N—(2,6-Dibromophenyl)-6,7-dihydro-5,6-dimethyl-7-thioxo-[1,2,4]triazolo[1,5-a]-[1,3,5]triazine-2-sulphonamide | mp: 312–314° C. |
| 10 | 6,7-Dihydro-5,6-dimethyl-7-thioxo-N—(2-trifluoromethylphenyl)-[1,2,4]triazolo-[1,5-a][1,3,5]triazine-2-sulphonamide | mp: 233–235° C. |
| 11 | 6,7-Dihydro-5,6-dimethyl-N—phenyl-7-thioxo-[1,2,4]triazolo[1,5-a]-[1,3,5]triazine-2-sulphonamide | mp: 231–233° C. |
| 12 | N—(2-Chlorophenyl)-6,7-dihydro-5,6-dimethyl- | mp: 200–206° C. |

-continued

| Example | Name of Compound | Physical Constant |
|---|---|---|
| | 7-thioxo-[1,2,4]triazolo[1,5-a]-[1,3,5]triazine-2-sulphonamide | |
| 13 | 6,7-Dihydro-N—(2-methoxyphenyl)-5,6-dimethyl-7-thioxo-[1,2,4]triazolo-[1,5-a][1,3,5]triazine-2-sulphonamide | mp: 198–200° C. |
| 14 | N—(2,6-Dichloro-3-methylphenyl)-6,7-dihydro-5,6-dimethyl-7-oxo-[1,2,4]triazolo[1,5-a]-[1,3,5]triazine-2-sulphonamide | mp: 336–338° C. |
| 15 | 6,7-Dihydro-5,6-dimethyl-N—(2-methyl-6-nitrophenyl)-7-oxo-[1,2,4]triazolo-[1,5-a][1,3,5]triazine-2-sulphonamide | |
| 16 | N—(2-Chloro-6-fluorophenyl)-6,7-dihydro-5,6-dimethyl-7-oxo-[1,2,4]triazolo[1,5-a]-[1,3,5]triazine-2-sulphonamide | mp: 304–306° C. |
| 17 | N—(2,6-Difluorophenyl)-6,7-dihydro-5,6-dimethyl-7-oxo-[1,2,4]triazolo[1,5-a]-[1,3,5]triazine-2-sulphonamide | mp: 298–300° C. |
| 18 | N—(2,6-Dibromophenyl)-6,7-dihydro-5,6-dimethyl-7-oxo-[1,2,4]triazolo-[1,5-a][1,3,5]triazine-2-sulphonamide | mp: 327–332° C. |
| 19 | 6,7-Dihydro-5,6-dimethyl-7-oxo-N—(2-trifluoromethylphenyl)-[1,2,4]triazolo-[1,5-a][1,3,5]triazine-2-sulphonamide | mp: 268–270° C. |
| 20 | 6,7-Dihydro-5,6-dimethyl-N—phenyl-7-oxo-[1,2,4]-triazolo[1,5-a]-[1,3,5]triazine-2-sulphonamide | |
| 21 | N—(2-Chlorophenyl)-6,7-dihydro-5,6-dimethyl-7-oxo-[1,2,4]triazolo-[1,5-a][1,3,5]triazine-2-sulphonamide | mp: 202–206° C. |
| 22 | 6,7-Dihydro-N—(2-methoxyphenyl)-5,6-dimethyl-7-oxo-[1,2,4]triazolo[1,5-a]-[1,3,5]triazine-2-sulphonamide | mp: 358–359° C. |
| 23 | N—(2,6-Dichlorophenyl)-6-ethyl-6,7-dihydro-5-methyl-7-thioxo-[1,2,4]-triazolo[1,5-a][1,3,5]triazine-2-sulphonamide, triethylammonium salt | mp: 179–180° C. |
| 24 | N—(2,6-Dichlorophenyl)-6-ethyl-6,7-dihydro-5-methyl-7-oxo-[1,2,4]-triazolo[1,5-a][1,3,5]triazine-2-sulphonamide, triethylammonium salt | mp: 185–186° C. |
| 25 | N—(2,6-Dichlorophenyl)-6,7-dihydro-5-methyl-6-phenyl-7-thioxo-[1,2,4]-triazolo[1,5-a][1,3,5]triazine-2-sulphonamide, triethylammonium salt | mp: 233–235° C. |
| 26 | N—(2,6-Dichlorophenyl)-6,7-dihydro-5-methyl-6-phenyl-7-oxo-[1,2,4]-triazolo[1,5-a][1,3,5]triazine-2-sulphonamide | mp: 298–300° C. |
| 27 | N—(2,6-Dichlorophenyl)-6,7-dihydro-6-methyl-7-thioxo-[1,2,4]triazolo-[1,5-a][1,3,5]triazine-2-sulphonamide | |
| 28 | N—(2,6-Dichlorophenyl)-6,7-dihydro-6-methyl-7-oxo-[1,2,4]triazolo-[1,5-a][1,3,5]triazine-2-sulphonamide | mp: 296–300° C. |
| 29 | N—(2,6-Dichlorophenyl)-6-ethyl-6,7-dihydro-7-thioxo-[1,2,4]triazolo-[1,5-a][1,3,5]triazine-2-sulphonamide | |
| 30 | N—(2,6-Dichlorophenyl)-6-ethyl-6,7-dihydro-7-oxo-[1,2,4]triazolo-[1,5-a][1,3,5]triazine-2-sulphonamide | mp: 285–287° C. |
| 31 | N—(2,6-Dichlorophenyl)-6,7-dihydro-6-phenyl-7-thioxo-[1,2,4]triazolo-[1,5-a][1,3,5]triazine-2-sulphonamide | |
| 32 | N—(2,6-Dichlorophenyl)-6,7-dihydro-6-phenyl-7-oxo-[1,2,4]triazolo-[1,5-a][1,3,5]triazine-2-sulphonamide | mp: 262–265° C. |
| 33 | N—(2,6-Dichlorophenyl)-5-ethyl-6,7-dihydro-6-methyl-7-thioxo-[1,2,4]triazolo-[1,5-a][1,3,5]triazine-2-sulphonamide, triethylammonium salt | mp: 260–262° C. |
| 34 | N—(2,6-Dichlorophenyl)-5-ethyl-6,7-dihydro-6-methyl-7-oxo-[1,2,4]triazolo-[1,5-a][1,3,5]triazine-2-sulphonamide, triethylammonium salt | mp: 288–291° C. |
| 35 | N—(2,6-Dichlorophenyl)-5,6-diethyl-6,7-dihydro-7-thioxo-[1,2,4]triazolo-[1,5-a][1,3,5]triazine-2-sulphonamide, triethylammonium salt | mp: 185–187° C. |
| 36 | N—(2,6-Dichlorophenyl)-5,6-diethyl-6,7-dihydro-7-oxo-[1,2,4]triazolo-[1,5-a][1,3,5]triazine-2-sulphonamide, | mp: 277–280° C. |

-continued

| Example | Name of Compound | Physical Constant |
|---|---|---|
| | triethylammonium salt | |
| 37 | N—(2,6-Dichlorophenyl)-5-ethyl-6,7-dihydro-6-phenyl-7-thioxo-[1,2,4]triazolo-[1,5-a][1,3,5]triazine-2-sulphonamide, triethylammonium salt | mp: 219–221° C. |
| 38 | N—(2,6-Dichlorophenyl)-5-ethyl-6,7-dihydro-6-phenyl-7-oxo-[1,2,4]triazolo-[1,5-a][1,3,5]triazine-2-sulphonamide, triethylammonium salt | mp: 291–293° C. |
| 39 | N—(2,6-Dichlorophenyl)-6,7-dihydro-6-methyl-5-phenyl-7-thioxo-[1,2,4]triazolo-[1,5-a][1,3,5]triazine-2-sulphonamide, hydrate | mp: 270–272° C. |
| 40 | N—(2,6-Dichlorophenyl)-6,7-dihydro-6-methyl-5-phenyl-7-oxo-[1,2,4]triazolo-[1,5-a][1,3,5]triazine-2-sulphonamide, triethylammonium salt | mp: 201–203° C. |
| 41 | N—(2,6-Dichlorophenyl)-6-ethyl-6,7-dihydro-5-phenyl-7-thioxo-[1,2,4]triazolo-[1,5-a][1,3,5]triazine-2-sulphonamide | |
| 42 | N—(2,6-Dichlorophenyl)-6-ethyl-6,7-dihydro-5-phenyl-7-oxo-[1,2,4]triazolo-[1,5-a][1,3,5]triazine-2-sulphonamide, triethylammonium salt | mp: 209–212° C. |
| 43 | N—(2,6-Dichlorophenyl)-6,7-dihydro-5,6-diphenyl-7-thioxo-[1,2,4]triazolo-[1,5-a][1,3,5]triazine-2-sulphonamide | |
| 44 | N—(2,6-Dichlorophenyl)-6,7-dihydro-5,6-diphenyl-7-oxo-[1,2,4]triazolo-[1,5-a][1,3,5]triazine-2-sulphonamide, triethylammonium salt | mp: 225–227° C. |
| 45 | N—(2,6-Dichlorophenyl)-N—ethyl-6,7-dihydro-5,6-dimethyl-7-oxo-[1,2,4]triazolo-[1,5-a][1,3,5]triazine-2-sulphonamide | mp: 286–288° C. |
| 46 | N—(2,6-Dichlorophenyl)-6,7-dihydro-N,5,6-trimethyl-7-thioxo-[1,2,4]triazolo-[1,5-a][1,3,5]triazine-2-sulphonamide | mp: 296–298° C. |
| 47 | N—(2,6-Dichlorophenyl)-6,7-dihydro-5,6-dimethyl-7-oxo-[1,2,4]triazolo-[1,5-a][1,3,5]triazine-2-sulphonamide, triethylammonium salt | mp: 298–300° C. |
| 48 | N—(2,6-Dichlorophenyl)-6,7-dihydro-5,6-dimethyl-7-thioxo-[1,2,4]triazolo-[1,5-a][1,3,5]triazine-2-sulphonamide, sodium salt | |
| 49 | N—(2,6-Dichloro-3-methylphenyl)-6,7-dihydro-5,6-dimethyl-7-thioxo-[1,2,4]triazolo-[1,5-a][1,3,5]triazine-2-sulphonamide, triethylammonium salt | mp: 208–210° C. |
| 50 | N—(2-Chloro-6-fluorophenyl)-6,7-dihydro-5,6-dimethyl-7-thioxo-[1,2,4]triazolo-[1,5-a][1,3,5]triazine-2-sulphonamide, triethylammonium salt | mp: 173–175° C. |
| 51 | N—(2,6-Difluorophenyl)-6,7-dihydro-5,6-dimethyl-7-thioxo-[1,2,4]triazolo-[1,5-a][1,3,5]triazine-2-sulphonamide, triethylammonium salt | mp: 188–190° C. |
| 52 | N—(2,6-Dibromophenyl)-6,7-dihydro-5,6-dimethyl-7-thioxo-[1,2,4]triazolo-[1,5-a][1,3,5]triazine-2-sulphonamide, triethylammonium salt | mp: 301–305° C. |
| 53 | 6,7-Dihydro-5,6-dimethyl-N—(2-methyl-6-nitrophenyl)-7-thioxo-[1,2,4]triazolo-[1,5-a][1,3,5]triazine-2-sulphonamide, triethylammonium salt | mp: 193–195° C. |
| 54 | 6,7-Dihydro-5,6-dimethyl-7-thioxo-N—(2-trifluoromethylphenyl)-[1,2,4]triazolo-[1,5-a][1,3,5]triazine-2-sulphonamide, triethylammonium salt | mp: 209–211° C. |
| 55 | N—(2,6-Dichloro-3-methylphenyl)-6,7-dihydro-5,6-dimethyl-7-oxo-[1,2,4]triazolo-[1,5-a][1,3,5]triazine-2-sulphonamide, triethylammonium salt | mp: 306–309° C. |
| 56 | N—(2-Chloro-6-fluorophenyl)-6,7-dihydro-5,6-dimethyl-7-oxo-[1,2,4]triazolo-[l,5-a][l,3,5]triazine-2-sulphonamide, triethylammonium salt | mp: 301–303° C. |
| 57 | N—(2,6-Difluorophenyl)-6,7-dihydro-5,6-dimethyl-7-oxo-[1,2,4]triazolo-[1,5-a][1,3,5]triazine-2-sulphonamide, triethylammonium salt | mp: 300–302° C. |

-continued

| Example | Name of Compound | Physical Constant |
|---|---|---|
| 58 | 6,7-Dihydro-N—(2-iodophenyl)-5,6-dimethyl-7-oxo-[1,2,4]triazolo-[1,5-a][1,3,5]triazine-2-sulphonamide | mp: 213–218° C. |
| 59 | N—(2-Chloro-6-methylphenyl)-6,7-dihydro-5,6-dimethyl-7-oxo-[1,2,4]triazolo-[1,5-a][1,3,5]triazine-2-sulphonamide, triethylammonium salt | mp: 250–252° C. |
| 60 | N—(2-Bromophenyl)-6,7-dihydro-5,6-dimethyl-7-thioxo-[1,2,4]triazolo-[1,5-a][1,3,5]triazine-2-sulphonamide | mp: 188–190° C. |
| 61 | N—(2-Chloro-6-methylphenyl)-6,7-dihydro-5,6-dimethyl-7-thioxo-[1,2,4]triazolo-[1,5-a][1,3,5]triazine-2-sulphonamide | mp: 266–267° C. |
| 62 | N—(2-Chloro-6-methylphenyl)-6,7-dihydro-5,6-dimethyl-7-thioxo-[1,2,4]triazolo-[1,5-a][1,3,5]triazine-2-sulphonamide, triethylammonium salt | mp: 240–242° C. |
| 63 | N—(2-Chloro-6-ethylphenyl)-6,7-dihydro-5,6-dimethyl-7-thioxo-[1,2,4]triazolo-[1,5-a][1,3,5]triazine-2-sulphonamide | mp: 246–248° C. |
| 64 | N—(2-Ethoxycarbonylphenyl)-6,7-dihydro-5,6-dimethyl-7-thioxo-[1,2,4]triazolo-[1,5-a][1,3,5]triazine-2-sulphonamide | mp: 163–165° C. |
| 65 | 6,7-Dihydro-5,6-dimethyl-N—(2-methylthiophenyl)-7-thioxo-[1,2,4]triazolo[1,5-a]-[1,3,5]triazine-2-sulphonamide, hydrate | mp: 140–141° C. |
| 66 | N—(2-Ethoxycarbonyl-6-methylphenyl)-6,7-dihydro-5,6-dimethyl-7-thioxo-[1,2,4]triazolo[1,5-a][1,3,5]triazine-2-sulphonamide | mp: 168–170° C. |
| 67 | 6,7-Dihydro-5,6-dimethyl-N—(2,3-dimethyl-6-nitrophenyl)-7-thioxo-[1,2,4]-triazolo-[1,5-a][1,3,5]triazine-2-sulphonamide, hydrate | mp: 281–283° C. |
| 68 | 6,7-Dihydro-N—(2-methoxycarbonyl-6-methylphenyl)-5,6-dimethyl-7-thioxo-[1,2,4]triazolo-[1,5-a][1,3,5]triazine-2-sulphonamide | mp: 212–213° C. |
| 69 | N—(2-Bromophenyl)-6,7-dihydro-5,6-dimethyl-7-thioxo-[1,2,4]triazolo-[1,5-a][1,3,5]triazine-2-sulphonamide | mp: 183–187° C. |
| 70 | 6,7-Dihydro-N—(2-methoxycarbonylphenyl)-5,6-dimethyl-7-oxo-[1,2,4]triazolo]-[1,5-a][1,3,5]triazine-2-sulphonamide | mp: 244–246° C. |
| 71 | N—(2-Ethoxycarbonylphenyl)-6,7-dihydro-5,6-dimethyl-7-oxo-[1,2,4]triazolo-[1,5-a][1,3,5]triazine-2-sulphonamide | mp: 233–236° C. |
| 72 | 6,7-Dihydro-N—(2-isopropoxycarbonylphenyl)-5,6-dimethyl-7-oxo-[1,2,4]triazolo]-[1,5-a][1,3,5]triazine-2-sulphonamide | mp: 244–246° C. |
| 73 | N—(2-Chloro-6-ethylphenyl)-6,7-dihydro-5,6-dimethyl-7-oxo-[1,2,4]triazolo-[1,5-a][1,3,5]triazine-2-sulphonamide | mp: 275–277° C. |
| 74 | N—(2-Acetylphenyl)-6,7-dihydro-5,6-dimethyl-7-oxo-[1,2,4]triazolo-[1,5-a][1,3,5]triazine-2-sulphonamide | mp: 225–227° C. |
| 75 | 6,7-Dihydro-N—(2-isopropyl-6-methylphenyl)-5,6-dimethyl-7-oxo-[1,2,4]triazolo]-[1,5-a][1,3,5]triazine-2-sulphonamide | mp: 284–285° C. |
| 76 | 6,7-Dihydro-N—(2-methoxycarbonyl-6-methylphenyl)5,6-dimethyl-7-oxo-[1,2,4]triazolo]-[1,5-a][1,3,5]triazine-2-sulphonamide | mp: 257–258° C. |
| 77 | 6,7-Dihydro-N—(2-isopropyl-6-methylphenyl)-5,6-dimethyl-N—(methylcarbamoyl)-7-oxo-[1,5-a][1,2,4]triazolo][1,3,5]triazine-2-sulphonamide | mp: 253–254° C. |
| 78 | N—(2-Fluorophenyl)-6,7-dihydro-5,6-dimethyl-7-oxo-[1,2,4]triazolo-[1,5-a][1,3,5]triazine-2-sulphonamide | mp: 229–231° C. |
| 79 | N—(2-Bromo-4-fluorophenyl)-6,7-dihydro-5,6-dimethyl-7-oxo-[1,2,4]triazolo[1,5-a]-[1,3,5]triazine-2-sulphonamide, hydrate | mp: 234–235° C. |
| 80 | N—(2,6-Dichlorophenyl)-6,7-dihydro-5-methyl-7-oxo-[1,2,4]triazolo-[1,5-a][1,3,5]triazine-2-sulphonamide | mp: 298–300° C. |
| 81 | 6,7-Dihydro-N—(2-iodophenyl)-5,6-dimethyl-7-thioxo-[1,2,4]triazolo]-[1,5-a][1,3,5]triazine-2-sulphonamide | mp: 192–194° C. |
| 82 | 6,7-Dihydro-N—(2-isopropyl-6-methylphenyl)-5,6-dimethyl-7-thioxo-[1,2,4]triazolo]-[1,5-a][1,3,5]triazine-2-sulphonamide | mp: 269–271° C. |
| 83 | N—(2-Bromo-6-chloro-4-fluorophenyl)- | mp: 271–273° C. |

| Example | Name of Compound | Physical Constant |
|---|---|---|
| | 6,7-dihydro-5,6-dimethyl-7-thioxo-[1,2,4]-triazolo[1,5-a][1,3,5]triazine-2-sulphonamide | |
| 34 | N—(2-Bromo-6-methoxy)-6,7-dihydro-5,6-dimethyl-7-thioxo-[1,2,4]triazolo-[1,5-a][1,3,5]triazine-2-sulphonamide | mp: 229–231° C. |
| 85 | 6,7-Dihydro-N—(2,6-dimethylphenyl)-5,6-dimethyl-7-thioxo-[1,2,4]triazolo]-[1,5-a][1,3,5]triazine-2-sulphonamide, hydrate | mp: 263–265° C. |
| 86 | 6,7-Dihydro-5,6-dimethyl-7-oxo-N—quinolin-8-yl-[1,2,4]triazolo]-[1,5-a][1,3,5]triazine-2-sulphonamide | mp: 240–242° C. |
| 87 | N—(4-Bromo-2,6-dichlorophenyl)-6,7-dihydro-5,6-dimethyl-7-thioxo-[1,2,4]-triazolo-[1,5-a][1,3,5]triazine-2-sulphonamide, hydrate | mp: 283–285° C. |
| 88 | 6,7-Dihydro-5,6-dimethyl-N—quinolin-8-yl-7-thioxo-[1,2,4]triazolo]-[1,5-a][1,3,5]triazine-2-sulphonamide | mp: 137–139° C. |
| 89 | 6,7-Dihydro-N—(2-methoxycarbonyl-3,6-dimethylphenyl)-5,6-dimethyl-7-thioxo-[1,2,4]triazolo]-[1,5-a][1,3,5]triazine-2-sulphonamide | mp: 222–224° C. |
| 90 | 6,7-Dihydro-N—(2-methoxycarbonyl-5,6-dimethylphenyl)-5,6-dimethyl-7-thioxo-[1,2,4]triazolo]-[1,5-a][1,3,5]triazine-2-sulphonamide | mp: 194–195° C. |
| 91 | N—(2-Bromo-6-chlorophenyl)-6,7-dihydro-5,6-dimethyl-7-thioxo-[1,2,4]-triazolo-[1,5-a][1,3,5]triazine-2-sulphonamide | mp: 304–305° C. |
| 92 | 6,7-Dihydro-N—(2-methoxycarbonyl-3,6-dimethylphenyl)-5,6-dimethyl-7-oxo-[1,2,4]triazolo]-[1,5-a][1,3,5]triazine-2-sulphonamide | mp: 225–227° C. |
| 93 | 6,7-Dihydro-N—(2-methoxycarbonyl-5,6-dimethylphenyl)-5,6-dimethyl-7-oxo-[1,2,4]triazolo]-[1,5-a][1,3,5]triazine-2-sulphonamide | mp: 216–218° C. |
| 94 | N—(2-Bromo-6-chlorophenyl)-6,7-dihydro-5,6-dimethyl-7-oxo-[1,2,4]-triazolo-[1,5-a][1,3,5]triazine-2-sulphonamide | mp: 321–322° C. |
| 95 | N—(2-Ethoxycarbonyl-6-methylphenyl)-6,7-dihydro-5,6-dimethyl-7-oxo-[1,2,4]-triazolo[1,5-a][1,3,5]triazine-2-sulphonamide | mp: 195–197° C. |

The following examples illustrate the posibilities for areas of use of the compounds of the invention.

EXAMPLE A

In a greenhouse, the compounds given below were applied at a rate of 1.0 kg active ingredient/ha., suspended in 500 liters water/ha. to the test plants of the species Helianthus and Chrysatheum in pre- and post-emergent uses. The damage to the weeds was assessed three weeks after treatment, on a score of 0 to 4, in which:
- 0=no activity
- 1=medium growth check
- 2=heavy growth check
- 3=full growth check
- 4=total destruction It was shown that the compounds of Examples 1 to 14, 16 to 19, 21 to 26, 28, 30, 32 to 40, 43, 44 to 47 and 49 to 95 caused 100% (=4) destruction of the planets in this test both in pre- and post-emergent application to the test plants.

EXAMPLE B

Seeds of mono- and dicotyledonous wees as well as of the crops wheat (Triticum aestivum), barley (Hordeum distichum) and rice (Oryza sativa) were planted in pots with humus-containing sandy soil and covered with earth. In a greenhouse, the compounds of the invention given below, were applied as a suspension in 500 liters of water/ha at a rate of 0.1 kg of active compound/ha. to the upper soil layer before emergence of the plants.

After treatement the test pots were placed in a greenhouse and the test plants grown under good growth conditons. Four weeks after the treatment plant damage was assessed. Untreated contols were used for comparison.

As the table clearly shows all the weeds were destroyed without damage to the crop plants.

In the following table:
- 0=no activity
- 4=total destruction of the plant.
- Tr=*Triticum aestivum*
- Ho=*Hordeum distichum*
- Or=*Oryza sativa*
- Se=*Setaria sp.*
- He=*Helianthus sp.*
- =*Stellaria sp.*
- Ab=*Abutilon sp.*
- Vi=*Viola sp.*
- Br=*Brassica sp.*
- So=*Solanum sp.*
- Ma=*Matricaria sp.*
- Cy=*Cyperus sp.*
- Ec=*Echinochloa sp.*

| Compounds of invention | Tr | Ho | Or | Se | He | St | Ab | Vi | Br | So | Ma | Cy | Ec |
|---|---|---|---|---|---|---|---|---|---|---|---|---|---|
| Example 3 | 0 | 0 | 0 | 4 | 4 | 4 | 4 | 4 | 4 | 4 | 4 | 3 | 4 |
| Example 4 | 0 | 0 | 0 | 4 | 4 | 4 | 4 | 4 | 4 | 4 | 4 | 3 | 4 |
| Control | 0 | 0 | 0 | 0 | 0 | 0 | 0 | 0 | 0 | 0 | 0 | 0 | 0 |

EXAMPLE C

Seeds of mono- and dicotyledonous weeds as well as of the crops wheat (Triticum aestivum), barley (Hordeum distichum) and rice (Oryza sativa) were planted in pots with humus-containing sandy soil and covered with earth. In a greenhouse, the compounds of the invention given below, were applied as a suspension in 500 liters of water/ha at a rate of 0.1 kg of active compound/ha, to the upper soil layer before emergence of the plants.

After treatement the test pots were placed in a greenhouse and the test plants grown under good growth conditions. Two weeks after the treatment plant damage was assessed. Untreated contols were used for comparison.

As the table clearly shows all the weeds were destroyed without damage to the crop plants.

In the following table:
0 = no activity
4 = total destruction of the plant.
Tr = *Triticum aestivum*
Ho = *Hordeum distichum*
Or = *Oryza sativa*
Se = *Setaria sp.*
He = *Helianthus sp.*
St = *Stellaria sp.*
Ab = *Abutilon sp.*
Vi = *Viola sp.*
Br = *Brassica sp.*
So = *Solanum sp.*
Ma = *Matricaria sp.*
Cy = *Cyperus sp.*
Ec = *Echinochloa sp.*

| Compounds of invention | Tr | Ho | Or | Se | He | St | Ab | Vi | Br | So | Ma | Cy | Ec |
|---|---|---|---|---|---|---|---|---|---|---|---|---|---|
| Example 3 | 0 | 0 | 0 | 4 | 4 | 4 | 4 | 4 | 4 | 4 | 4 | 3 | 4 |
| Control | 0 | 0 | 0 | 0 | 0 | 0 | 0 | 0 | 0 | 0 | 0 | 0 | 0 |

EXAMPLE D

In a greenhouse, the compounds of the invention shown in the table were applied at the rates given. For this the compounds were applied in vessels containing 1500 ml. As test plants there were used *Echinochloa crus-galli, Fimbrystylis miliacea, Paspalum distichum* and *Cyperus difformis* in the 2 to 5 leaved stage. In the table the scores have the following meanings:
0 = no activity
1 = slight damage
2 = intermediate damage
3 = heavy damage
4 = total destruction
Ec = *Echinochloa crus-galli*
Fi = *Fimbrystylis miliacea*
Pa = *Paspalum distichum*
Cy = *Cyperus difformis*

| Compound of the invention | Water application ppm | Ec | Fi | Pa | Cy |
|---|---|---|---|---|---|
| Example 2 | 30 | 4 | 4 | 4 | 4 |
| Example 3 | 30 | 4 | 4 | 4 | 4 |

We claim:
1. 6,7-Dihydro-[1,2,4]triazolo[1,5-a][1,3,5]triazine-2-sulphonamide of formula I

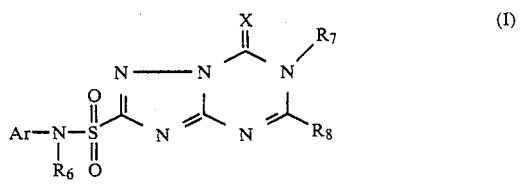

in which
Ar is a phenyl, naphthyl, pyridyl or thienyl group of formula

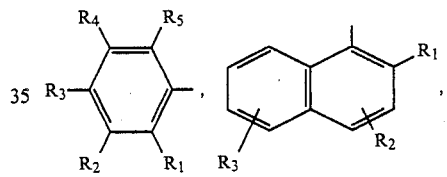

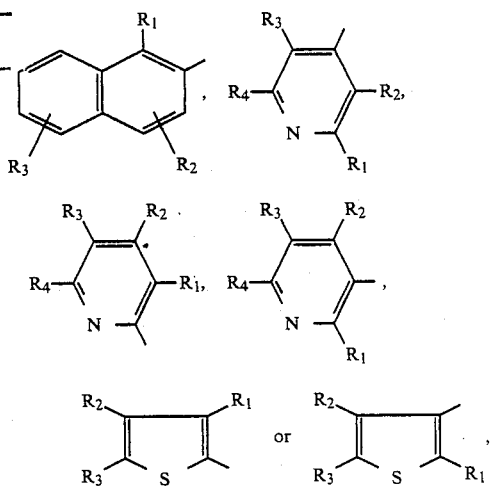

$R_1$, $R_2$, $R_3$, $R_4$ and $R_5$ are the same or different and are hydrogen, a $C_1$-$C_6$-alkyl, $C_2$-$C_6$-alkenyl or $C_2$-$C_6$-alkynyl group, each of which is optionally substituted by one or more of the same or different halo, hydroxy, halo-$C_1$-$C_4$-alkyl, $C_1$-$C_4$-alkoxy, halo-$C_1$-$C_4$-alkoxy, $C_1$-$C_4$-alkylthio, $C_1$-$C_4$-alkylsulphinyl or $C_1$-$C_4$-alkylsulphonyl, halogen, $C_1$-$C_4$-alkoxy, a group $R_9$—O—CO, a carbamoyl group

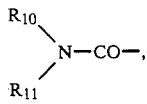

an amino group

cyano, nitro, a sulphur containing group $R_9$—$S(O)_n$—, an acyl group $R_9$—CO, a group $R_9$—O—CO—$(CH_2)_n$, or phenyl or phenoxy, both of which are optionally substituted by one or more of $C_1$-$C_4$-alkyl, halo or nitro, $R_6$ is hydrogen, an acyl group $R_9$—CO, a group $R_9$—O—CO—, $C_1$-$C_6$-alkyl, $C_2$-$C_6$-alkenyl, $C_2$-$C_6$-alkynyl, phenyl-$C_1$-$C_4$-alkyl, a carbamoyl group ,

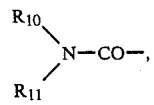

an alkali metal atom, a single metal equivalent of an alkaline earth or other metals or ammonium group, optionally substituted by $C_1$-$C_6$-alkyl, $R_7$ and $R_8$ are the same or different and are hydrogen, a $C_1$-$C_6$-alkyl, $C_2$-$C_6$-alkenyl or $C_2$-$C_6$-alkynyl group, each of which is optionally substituted by halo and/or $C_1$-$C_4$-alkoxy, a phenyl-$C_1$-$C_6$-alkyl, phenyl-$C_2$-$C_6$-alkenyl or phenyl-$C_2$-$C_6$-alkynyl group, each of which is optionally substituted by halo, $C_1$-$C_4$-alkyl, $C_1$-$C_4$-alkoxy, $C_1$-$C_4$-alkoxy-$C_1$-$C_4$-alkyl or halo-$C_1$-$C_4$-alkyl, phenyl, substituted by $R_1$, $R_2$, $R_3$, $R_4$ and $R_5$, an acyl group $R_9$—CO, a group $R_9$—O—CO, a group $R_9$—O—CO—$(CH_2)_n$, a carbamoyl group

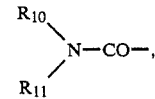

or a sulphonyl group $R_9$—$SO_2$, $R_9$ is hydrogen, a $C_1$-$C_6$-alkyl, $C_2$-$C_6$-alkenyl, $C_2$-$C_6$-alkynyl or phenyl-$C_1$-$C_4$-alkyl group, each of which is optionally substituted by one or more of the same or different halo, hydroxy or $C_1$-$C_4$-alkoxy, or phenyl, optionally substituted by halo, nitro or $C_1$-$C_4$-alkyl, $R_{10}$ and $R_{11}$ are the same or different and are hydrogen, a $C_1$-$C_6$-alkyl, $C_2$-$C_6$-alkenyl or $C_2$-$C_6$-alkynyl group, each of which is optionally substituted by one or more of the same or different halo, hydroxy or $C_1$-$C_4$-alkoxy, or $R_{10}$ and $R_{11}$ together with the adjacent nitrogen form a pyrrolidinyl, piperidino or morpholino ring, X is oxygen or sulphur, and n is 0, 1, or 2.

2. A herbicidal and plant-growth regulant composition which comprises a herbicidal and regulant effective amount of a compound according to claim 1, in admixture with carriers and diluents.

3. A method of combatting weeds which comprises applying to the weeds or their locus an herbicially effective amount of a compound according to claim 1.

4. A method of regulating the growth of plants which comprises applying to the plants or their locus a plant growth regulant amount of a compound according to claim 1.

5. 6,7-Dihydro-[1,2,4]triazolo[1,5-a][1,3,5]triazine-2-sulphonamide according to claim 1, in which Ar is a phenyl group of formula

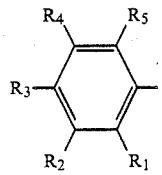

$R_1$ and $R_5$ are the same or different and are halogen, methyl, trifluoromethyl, nitro, methoxy or methoxycarbonyl, $R_2$, $R_3$ and $R_4$ are the same or different and are hydrogen, halogen, trifluoromethyl or a $C_1$-$C_4$-alkyl group, $R_6$ is hydrogen, a single equivalent of a metal or a $C_1$-$C_4$-acyl group, and $R_7$ and $R_8$ are the same or different and are hydrogen, $C_1$-$C_4$-acyl, $C_1$-$C_6$-alkyl, $C_2$-$C_4$-alkenyl or phenyl.

6. A herbicidal and plant-growth regulant composition which comprises a herbicidal and regulant effective amount of a compound according to claim 2, in admixture with carriers and diluents.

7. A method of combatting weeds which comprises applying to the weeds or their locus an herbicidally effective amount of a compound according to claim 2.

8. A method of regulating the growth of plants which comprises applying to the plants or their locus a plant growth regulant amount of a compound according to claim 2.

9. 6,7-Dihydro-[1,2,4]triazolo[1,5 a][1,3,5]triazine-2sulphonamide according to claim 2, in which $R_1$ and $R_5$ are halogen, $R_2$ is hydrogen or alkyl, $R_3$, $R_4$ and $R_6$ are hydrogen and $R_7$ and $R_8$ are alkyl.

10. A herbicidal and plant-growth regulant composition which comprises a herbicidal and regulant effective amount of a compound according to claim 9, in admixture with carriers and diluents.

11. A method of combattiang weeds which comprises applying to the weeds or their locus an herbicidally effective amount of a compound according to claim 9.

12. A method of regulating the growth of plants which comprises applying to the plants or their locus a plant growth regulant amount of a compound according to claim 9.

13. 6,7-Dihydro-[1,2,4]triazolo[1,5-a][1,3,5]triazine-2-sulphonamide according to claim 9, in which $R_4$ and $R_5$ are chlorine, $R_2$ is hydrogen or methyl and $R_7$ and $R_8$ are methyl.

14. A herbicidal and plant-growth regulant composition which comprises a herbicidal and regulant effective amount of a compound according to claim 13, in admixture with carriers and diluents.

15. A method of combatting weeds which comprises applying to the weeds or their locus an herbicidally effective amount of a compound according to claim 13.

16. A method of regulating the growth of plants which comprises applying to the plants or their locus a plant growth regulant amount of a compound according to claim 13.

17. 6,7-Dihydro-[1,2,4]triazolo[1,5-a][1,3,5]triazine-2-sulphonamide according to claim 13, in which $R_2$ is methyl and X is sulphur.

18. A herbicidal and plant-growth regulant composition which comprises a herbicidal and regulant effective amount of a compound according to claim 9, in admixture with carriers and diluents.

19. A method of combatting weeds which comprises applying to the weeds or their locus an herbicidally effective amount of a compound according to claim 18.

20. A method of regulating the growth of plants which comprises applying to the plants or their locus a plant growth regulant amount of a compound according to claim 18.

* * * * *